(12) United States Patent
Kolb et al.

(10) Patent No.: US 11,071,526 B2
(45) Date of Patent: Jul. 27, 2021

(54) SPECIMEN COLLECTION AND DELIVERY APPARATUS

(71) Applicant: PerkinElmer Health Sciences, Inc., Waltham, MA (US)

(72) Inventors: Andrew Kolb, Seattle, WA (US); Alan K. Lofquist, Kirkland, WA (US); C. Frederick Battrell, Wenatchee, WA (US)

(73) Assignee: PERKINELMER HEALTH SCIENCES, INC., Waltham, MA (US)

( * ) Notice: Subject to any disclaimer, the term of this patent is extended or adjusted under 35 U.S.C. 154(b) by 747 days.

(21) Appl. No.: 15/569,701

(22) PCT Filed: Apr. 29, 2016

(86) PCT No.: PCT/US2016/030194
§ 371 (c)(1),
(2) Date: Oct. 26, 2017

(87) PCT Pub. No.: WO2016/176613
PCT Pub. Date: Nov. 3, 2016

(65) Prior Publication Data
US 2018/0125464 A1    May 10, 2018

Related U.S. Application Data

(60) Provisional application No. 62/154,509, filed on Apr. 29, 2015.

(51) Int. Cl.
*A61B 10/00* (2006.01)
*B01L 3/00* (2006.01)
(Continued)

(52) U.S. Cl.
CPC ...... *A61B 10/0096* (2013.01); *A61B 10/0045* (2013.01); *A61B 10/02* (2013.01);
(Continued)

(58) Field of Classification Search
None
See application file for complete search history.

(56) References Cited

U.S. PATENT DOCUMENTS 4,978,504 A * 12/1990 Nason ................ A61B 10/0096
422/411
5,979,669 A    11/1999 Kitajima et al.
(Continued)

FOREIGN PATENT DOCUMENTS

CN    103957794 A    7/2014
CN    104284984 A    1/2015
(Continued)

*Primary Examiner* — Etsub D Berhanu
(74) *Attorney, Agent, or Firm* — Seed Intellectual Property Law Group LLP

(57) ABSTRACT

A specimen collection and delivery apparatus for collecting clinical specimens and delivery of samples thereof to, e.g., microfluidic testing devices for diagnostic analysis is disclosed. The specimen collection and delivery apparatus includes a closure housing for coupling with a sample tube at one end, an open luer for coupling with a complementary luer on a microfluidic device at the other end, and a filter matrix disposed in the interior. The filter matrix is air permeable and liquid impermeable at atmospheric pressure and prevents sample from flowing through the open luer end when coupled to a sample tube containing a specimen. Under vacuum, the liquid sample fraction of the specimen can be drawn through the filter matrix and into the microfluidic testing device through the luer connection for diagnostic analysis.

16 Claims, 8 Drawing Sheets

(51) Int. Cl.
*A61B 10/02* (2006.01)
*G01N 1/00* (2006.01)

(52) U.S. Cl.
CPC ............ *B01L 3/50825* (2013.01); *G01N 1/00* (2013.01); *B01L 2200/026* (2013.01); *B01L 2200/027* (2013.01); *B01L 2200/16* (2013.01); *B01L 2300/043* (2013.01); *B01L 2300/044* (2013.01); *B01L 2300/0681* (2013.01); *B01L 2400/0683* (2013.01)

(56) References Cited

U.S. PATENT DOCUMENTS

| | | | |
|---|---|---|---|
| 6,155,991 | A | 12/2000 | Beat et al. |
| 8,835,146 | B2 | 9/2014 | Battrell et al. |
| 8,921,085 | B2 | 12/2014 | Battrell et al. |
| 2005/0010189 | A1 | 1/2005 | Toomey et al. |
| 2007/0015140 | A1 | 1/2007 | Kobori et al. |
| 2009/0084202 | A1 | 4/2009 | Mimori et al. |
| 2009/0088336 | A1* | 4/2009 | Burd .................. G01N 33/5304 506/9 |
| 2009/0269246 | A1 | 10/2009 | Hasegawa |
| 2011/0144593 | A1 | 6/2011 | Fremming et al. |
| 2011/0194977 | A1* | 8/2011 | Miyamura ........ B01L 3/502738 422/68.1 |
| 2012/0141341 | A1* | 6/2012 | Bartfeld ................ B01L 3/5082 422/550 |
| 2013/0288234 | A1 | 10/2013 | Harris et al. |
| 2013/0288358 | A1 | 10/2013 | Handique |
| 2015/0353919 | A1 | 12/2015 | Mielke et al. |

FOREIGN PATENT DOCUMENTS

| | | |
|---|---|---|
| EP | 1 867 972 A1 | 12/2007 |
| EP | 2 529 837 A2 | 12/2012 |
| JP | 63-112974 A | 5/1988 |
| JP | 2007-509633 A | 4/2007 |
| JP | 2007-183170 A | 7/2007 |
| JP | 2007-218903 A | 8/2007 |
| JP | 2010-008217 A | 1/2010 |
| JP | 2011-069778 A | 4/2011 |
| JP | 2011-180117 A | 9/2011 |
| JP | 2013-011594 A | 1/2013 |
| JP | 2013-533979 A | 8/2013 |
| JP | 2013-245993 A | 12/2013 |
| WO | 2005/042784 A2 | 5/2005 |
| WO | 2012/007503 A1 | 1/2012 |

\* cited by examiner

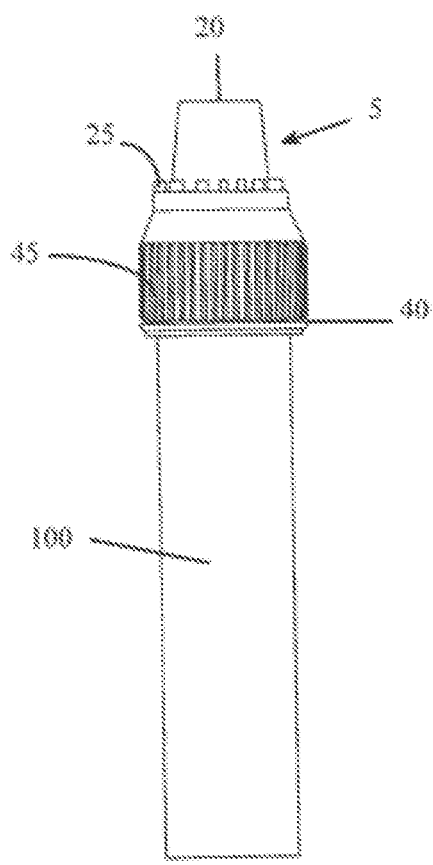
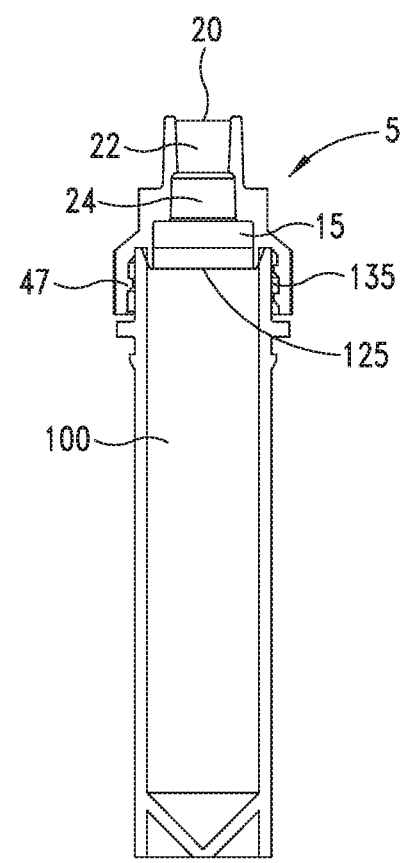
FIG. 3A
FIG. 3B

SPECIMEN COLLECTION AND DELIVERY APPARATUS

FIELD OF THE DISCLOSURE

This disclosure relates to various embodiments of a specimen collection and delivery apparatus for collecting clinical specimens and delivery of samples thereof to microfluidic testing devices for diagnostic analysis.

BACKGROUND OF THE DISCLOSURE

The art relating to collection, transport, and delivery of clinical samples for diagnostic analysis is well-established, but remains in need of improvement, both to ensure the integrity of the clinical sample and its protection from contamination, but also to ensure that healthcare professionals are not unnecessarily or inadvertently exposed to hazardous biological materials. Moreover, there is a clear and ongoing interest\in microfluidic devices for clinical and veterinary diagnostic assays. As these commercial applications increase, the world-to-chip interface is receiving increasing attention, however, little has been done in the area of sample collection to both improve the validity of diagnostic analysis by preventing cross-sample contamination, and just as importantly, to prevent exposure of those persons handling the specimens to objectionable or potentially infectious materials. Furthermore, awareness of the dangers of unsafe handing of biological fluids and specimens has increased dramatically in the last two decades, and single entry devices are increasingly needed that seamlessly integrate sample preparation, extraction, and analysis without unnecessary operator exposure. A further objective is the need to fully integrate the device into a disposable format, so that once a sample is collected, either by patient or by a health professional, all remaining steps of the analysis, up to and including display of the result, are performed without further personal exposure to the sample. A critical step in this process is thus the design of a completely closed system in which the end-user is protected from exposure to sample material at each step of sample preparation and analysis, and to our knowledge, satisfactory solutions to this problem have not been recognized or brought forward prior to our disclosure herein.

SUMMARY OF THE DISCLOSURE

According to a first aspect of the invention, a sample collection and delivery apparatus includes a closure housing including a base portion configured for selective removable coupling to a sample tube, a tapered mid portion, and an open luer end configured for receiving a complementary luer of a test device; and a filter matrix disposed therein. In one embodiment, the filter matrix is air permeable and liquid impermeable at atmospheric pressure and configured to block the flow of sample through the open luer end. In another embodiment, the filter matrix is air permeable and liquid permeable under reduced atmospheric pressure and configured to enable the flow of sample though the open luer end. In another embodiment, the reduced atmospheric pressure is around one pound per square inch. In yet another embodiment, the filter matrix is disposed in the interior of the tapered mid portion. In some embodiments, the filter matrix is comprised of a porous material selected from the group consisting of a hydrophobic porous material, a hydrophilic porous material, an oleophobic porous material, and an oleophilic porous material. In one embodiment, the filter matrix is comprised of a hydrophobic porous material. In another embodiment, the hydrophobic porous material is a polymeric material. In other embodiments, the filter matrix has a pore size of from around 50 µm to around 100 µm and a thickness of around 1000 µm to around 2000 µm. In another embodiment, the filter matrix is impregnated with an internal assay control. In other embodiments, the internal assay control includes a natural nucleic acid sequence or a non-natural nucleic acid sequence. In another embodiment, the sample collection and delivery apparatus includes circumferential projections radially disposed between the tapered mid portion and the luer end. In another embodiment, the base portion includes an internal threaded portion configured for removable coupling with a complementary threaded portion of a sample tube. In yet another embodiment, the closure housing is selectively removably coupled to a sample tube. In another embodiment, the volume of the sample tube is around 2 mL.

In another aspect of the invention, a method of collecting and delivering a test sample to a microfluidic cartridge includes the steps of: obtaining a test sample from an individual suspected of having a condition; providing a sample tube with a first open end; disposing the test sample in the sample tube; coupling the sample collection and delivery apparatus as described above to the sample tube; inverting the sample tube; coupling the luer taper end of the sample collection and delivery apparatus to a complementary luer taper end on the microfluidic cartridge to create a luer channel; inserting the microfluidic cartridge into a host instrument; and instructing the host instrument to apply a vacuum to the luer channel.

In another aspect of the invention, a sample collection and delivery apparatus, includes a sample tube having an interior portion configured to contain a test specimen, an upper portion with an opening to the interior portion configured to receive the specimen, a lower portion with a first filter matrix disposed therein, and an open luer end opposite the opening to the interior portion, wherein the first filter matrix is configured to block the flow of the specimen through the open luer end; and a closure housing configured for sealing the opening, including a filter chamber with a second filter matrix disposed therein, a tab configured for user manipulation, a flexible hinge configured to couple the closure housing to the sample tube, and, optionally, a vent hole. In one embodiment, the first filter matrix is air permeable and liquid impermeable at atmospheric pressure. In another embodiment, the first filter matrix is air permeable and liquid permeable under reduced atmospheric pressure and configured to enable the flow of liquid specimen through the luer end. In yet another embodiment, the reduced atmospheric pressure is around one pound per square inch. In other embodiments, the filter matrix is comprised of a porous material selected from the group consisting of a hydrophobic porous material, a hydrophilic porous material, an oleophobic porous material, and an oleophilic porous material. In one embodiment, the filter matrix is a hydrophobic porous material. In yet another embodiment, the hydrophobic porous material is a polymeric material. In other embodiments, the first filter matrix has a pore size of from around 50 µm to around 100 µm and a thickness of around 1000 µm to around 2000 µm. In another embodiment, the first filter matrix is impregnated with an internal assay control. In some embodiments, the internal assay control includes a natural or a non-natural nucleic acid sequence. In another embodiment, sample collection and delivery apparatus further includes circumferential projections radially disposed between the lower portion and the luer end.

In another aspect of the invention, a method of collecting and delivering a test sample to a microfluidic cartridge, includes the steps of: obtaining a test specimen from an individual suspected of having a condition; disposing the test specimen in the sample collection and delivery apparatus as described above; coupling the luer taper end of the sample collection and delivery apparatus to a complementary luer taper end on the microfluidic cartridge to create a luer channel; inserting the microfluidic cartridge into a host instrument; and instructing the host instrument to apply a vacuum to the luer channel.

BRIEF DESCRIPTION OF THE DRAWINGS

FIG. 3A is a perspective side view of one embodiment of the sample collection and delivery apparatus of the present invention coupled with a sample tube.

FIG. 3B is a cross-sectional side view of an alternative embodiment of the sample collection and delivery apparatus of the present invention coupled with a sample tube.

DETAILED DESCRIPTION

The following detailed description is not to be taken in a limiting sense, but is made merely for the purpose of illustrating the general principles of the disclosure, since the scope of the disclosure is best defined by the appended claims.

Figure 1:
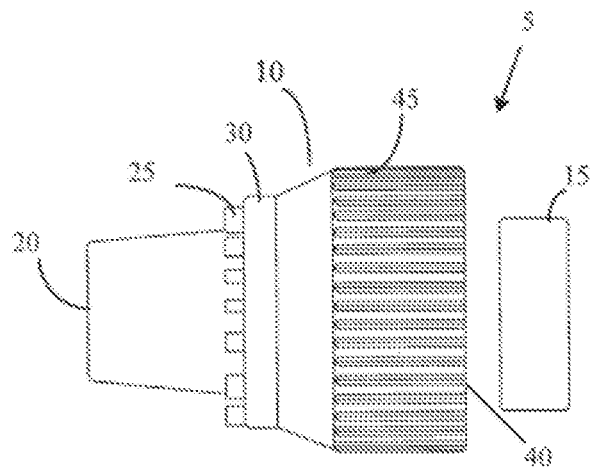
FIG. 1 is a perspective side view of one embodiment of the sample collection and delivery apparatus of the present invention.

Referring to FIG. 1, there is shown a perspective side view of an exemplary specimen collection and delivery apparatus 5 according to the present invention. The specimen collection and delivery apparatus 5 includes a closure housing 10 and a filter matrix 15. The closure housing can also be referred to as a "sample tube cap". Various components of the closure housing 10 can be constructed of clear or colored injection molded polymers. The closure housing 10 can be selectively removably coupled to a sample tube proximate a sample tube coupling end 40, and selectively removably coupled to a test device proximate an open luer taper end 20. The sample tube coupling end 40 can have any suitable size compatible with standard sample tubes used for collection and containment of a clinical specimen, such as capillary blood or other bodily fluid, for subsequent testing procedures and diagnostic analysis. In one embodiment, the sample tube coupling end 40 is sized to be compatible with a standard 2 mL FISHERBRAND™ "screwtop" tube. With continued reference to FIG. 1, the exemplary closure assembly has a generally conical shape with a base portion 45, a tapered mid-portion 30, and an open tapered luer end 20. A lateral external surface of the base portion 45 can include ribs, ridges, and/or other textured surfaces to facilitate manual gripping. The base portion 45 is configured to be coupled with a sample tube, while the luer end 20 is configured to be coupled to a microfluidic device, as further illustrated below. In one embodiment, the end of the tapered mid-portion 30 proximate to the luer end 20 can be radially disposed with circumferential ribbed projections 25. The number and positioning of the ribbed projections 25 is not obligatory to the invention and several possible alternatives of each are herein contemplated.

The filter matrix 15 is a generally porous, disc-shaped structure that is air permeable and liquid impermeable under ambient conditions. The filter matrix 15 can be constructed of porous materials with affinity for either aqueous or organic liquids. In some embodiments, the filter matrix is composed of a hydrophobic or a hydrophilic porous material. In other embodiments, the filter matrix is composed of an oleophobic (i.e. lipophobic) or an oleophilic (i.e. lipophilic) porous material. The skilled artisan will appreciate that the particular properties of the porous material will be application-dependent and determined by the specific samples or specimens intended for collection and analysis. In an exemplary embodiment, the filter matrix is constructed of hydrophobic porous material for collection of fecal samples for subsequent clinical analysis. Many suitable thicknesses and pore sizes of the filter matrix 15 are contemplated by the present invention. In some embodiments, the filter matrix can range from around 50 µm thick to around 2000 µm thick. In further embodiments, the filter matrix can range from around 1000 µm thick to around 2000 µm thick. In some embodiments, the pore size of the filter matrix can range from around 10 µm to around 200 µm. In yet other embodiments, the pore size of the filter matrix can range from around 50 µm to around 100 µm. In one exemplary embodiment, the filter matrix has a thickness of 1500 µm and a pore size of 50-90 µm. In other embodiments, the filter matrix can be "asymmetric" with a gradient of pore sizes that decrease from one end of the filter to the other. Such asymmetric filters can find use in filtering samples, e.g. whole blood, that contain cells, or particles, of different sizes. The porous matrix is typically composed of polymeric fibers known in the art, such as polyethylene, polypropylene, polyethylene terephthalate, polycarbonate, polystyrene, and the like. In some embodiments, the porous matrix can be composed of glass or ceramic fibers.

In operation, at atmospheric pressure, the filter matrix 15 blocks the flow of liquid into the open luer taper end 20 of the closure housing 10 and specimen material is retained in the sample tube. In contrast, application of vacuum force to the luer taper end draws the liquid phase of the specimen through the filter matrix into and through the open luer end. Any particulate matter larger than the pore size of the filter matrix is retained in the specimen collection and delivery apparatus, and is thus removed from the liquid sample. The amount of vacuum necessary to draw liquid sample through the filter matrix is dependent upon several parameters, including the surface properties of the porous material, the thickness of the filter matrix, and the pore size of the filter matrix. In one exemplary embodiment, a drop in atmospheric pressure ($\Delta p$) of one psi is sufficient to draw the liquid fraction of a fecal sample through a filter with a pore size of 50-90 μm and a thickness of 1.58 mm, e.g., a Porex X-4903 filter.

In some embodiments of the present invention, e.g., when the clinical specimen is intended for PCR-based molecular analysis, the filter matrix 15 may be impregnated with an internal assay control. Internal controls, also referred to as process or procedural controls, refer to a control target that is always present in the assayed sample or is added to the assay sample prior to, e.g., nucleic acid extraction. Internal controls are traditionally used to verify the functionality of the extraction, amplification and detection processes of a molecular analysis. According to the present invention, an internal control is impregnated in the filter matrix of the specimen collection and delivery apparatus. This arrangement offers the advantages of: 1) verifying that the end-user has properly connected the closure assembly to the sample tube containing the specimen, and 2) that liquid sample has been successfully drawn through the filter matrix and into the downstream diagnostic test system.

Internal control materials can be obtained commercially, prepared in-house, or obtained from other sources and can be purified natural nucleic acid, a purified non-natural nucleic acid in any suitable vector, such as a plasmid or phage, or an inactivated organism containing the target nucleic acid. Non-natural (i.e., synthetic) nucleic acid sequences can be particularly well-suited as alternatives to natural target sequence internal controls, as they can prevent false positive signals due to contamination from natural sources during manufacture, storage, and/or end-use. The internal control material can be impregnated into the filter matrix by adding a liquid formulation containing the control onto the filter matrix (e.g., printing) and allowing the formulation to dry by either freeze-drying (e.g., lyophilizing) the filter or placing the filter matrix in a low-humidity environment. In some embodiments, the formulated control may include additional excipients to, e.g., produce color upon rehydration. Any suitable formulation known in the art can be used in the practice of the present invention, including, but not limited to, those disclosed in U.S. Pat. Nos. 8,835,146 and 8,921,085, which are herein incorporated by reference in their entireties. The internal control can be constructed so that it is at a concentration near the lower limit of detection of the assay. The concentration should be high enough to provide consistent positive results but low enough to challenge the detection system near the limit of detection. Advantageously, by impregnating a known concentration, or titer, of internal control target into the filter matrix, the end-user can determine the sample extraction efficiency during real-time (RT)-PCR analysis.

Figure 2A:
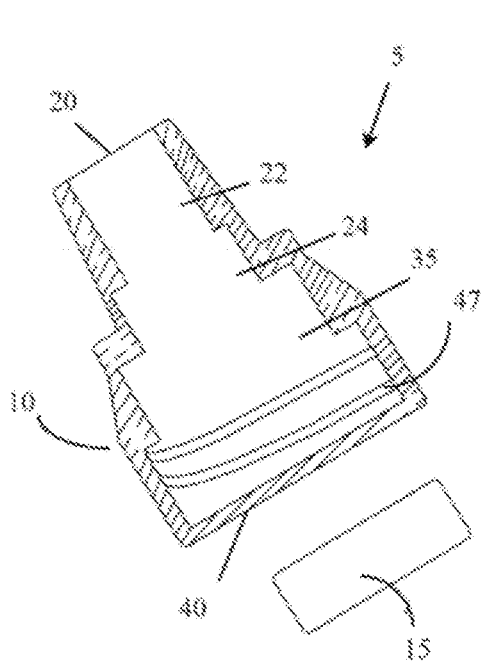
FIGS. 2A and 2B are cross-sectional side views of alternative embodiments of the sample collection and delivery apparatus of the present invention.
Figure 2B:
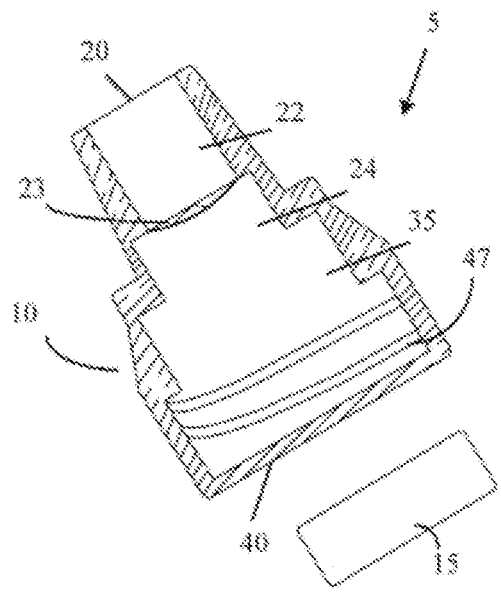

FIGS. 2A and 2B depict cross-sectional views of alternative embodiments of exemplary specimen collection and delivery apparatuses 5, according to the present invention. The base portion of the closure housing 10 includes internal threads 47, configured to be complementary to the threaded top of a standard sample tube. In other words, the specimen collection and delivery apparatus is threaded for releasable attachment to a "screwtop" sample tube. The interior portion of closure housing 10 can include a first (or "lower") sample channel 35 and a second (or "upper") sample channel 24, which are in fluid communication with each other. The first sample channel 35 is in further fluid communication with the sample tube coupling end 40 and the second sample channel is in further fluid communication with a luer lumen 22. Together, the first sample channel, second sample channel, and luer lumen form a continuous fluid path for liquid sample to flow from the sample tube through the closure assembly and into a test device. In practice, the filter matrix is disposed in the first sample channel 35 and functions to prevent the flow of liquid sample through the sample channels until a vacuum is applied to the luer end 20. In an alternative embodiment of the present invention, as depicted in FIG. 2B, the closure housing can include a septum 23 disposed between the luer lumen 22 and the second sample channel 24. The septum 23 is a burstable membrane that can be engraved, or cut, with a web pattern that is disrupted when the luer taper end 20 is fixedly coupled to a complementary, or mating, luer taper of a test device. In practice, bursting of the septum 23 provides audible and/or tactile feedback to the end-user when the closure housing 10 is operably coupled to a test device.

FIG. 3A is an external perspective view depicting the specimen collection and delivery apparatus 5 coupled to an exemplary sample tube 100. As described herein, the sample tube 100 may be any suitable container for receiving and retaining a clinical specimen for subsequent analysis, e.g., a PCR-based molecular diagnostic assay. In this embodiment, the sample tube is a standard 2 mL FISHERBRAND™ "screwtop" tube. FIG. 3B depicts a cross-sectional view of the specimen collection and delivery apparatus 5 coupled to an exemplary sample tube 100. The sample tube 100 includes an external threaded portion 135 disposed proximate an opening 125. An external threaded portion 135 is suitable for facilitating closure, or sealing, of the opening 125 when coupled with the complementary threaded portion 47 of the closure housing 10. In practice, when the specimen collection and delivery system is coupled to the sample tube 100, the filter matrix 15 functions as a barrier to selectively retain the sample in the sample tube and prevents any material from leaking into the second (or "upper") sample channel 24 of the closure housing. In this configuration, although the luer taper end 20 is open, the filter matrix prevents any specimen material from flowing into the luer lumen. The end-user is thus protected from exposure to the specimen during handling, delivery, and analysis procedures following closure of the sample tube with the specimen collection and delivery apparatus. In an alternative embodiment of the present invention, a burstable septum can be disposed between the second chamber 24 and the luer lumen 22 of the specimen collection and delivery system, as disclosed herein.

Figure 4A:
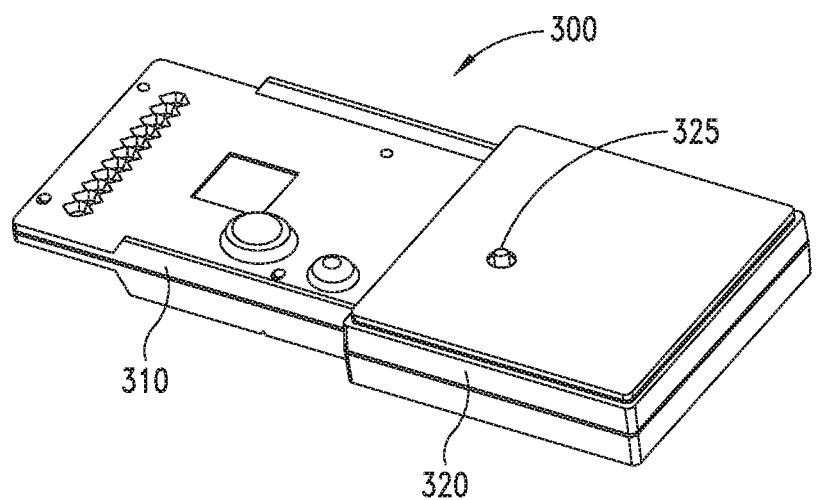
FIGS. 4A and 4B are perspective side views of one embodiment of the sample collection and delivery apparatus of the present invention coupled with a microfluidic device.
Figure 4B:
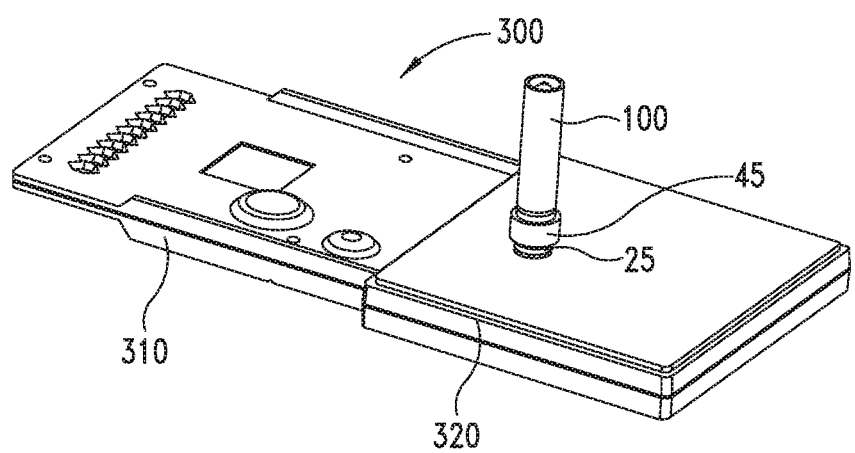

FIGS. 4A and 4B depict perspective views of a device 300, illustrating an exemplary use of the specimen collection and delivery apparatus 5 of the present invention. In this embodiment, the device 300 is a microfluidic cartridge with a first (or "outboard") portion 320, configured for sample preparation and a second (or "inboard") portion 310, configured for insertion into a docking bay of a host instrument, wherein the sample is further analyzed according to any of a number of diagnostic assay protocols known in the art. As depicted in FIG. 4A, the outboard portion 320 is provided with a projecting luer taper 325, configured for coupling with the complementary luer taper of the specimen collection and delivery apparatus described herein. FIG. 4B depicts the sample tube 100 in an inverted orientation in which the specimen collection and delivery system 5 is coupled to the device 300 by joining the complementary luers. In this configuration, the luer taper of the closure assembly is operably coupled to the projecting luer taper of the microfluidic cartridge to form a fluid channel for transferring liquid sample from the sample tube to the microfluidic cartridge, as described further below. In practice, the projecting ribs 25 of the closure assembly contact the outboard portion of the microfluidic cartridge and function to prevent damage to the specimen collection and delivery apparatus and/or to the cartridge, e.g., due to excessive force exerted by the end-user when connecting the capped sample tube to the cartridge.

Figure 5A:
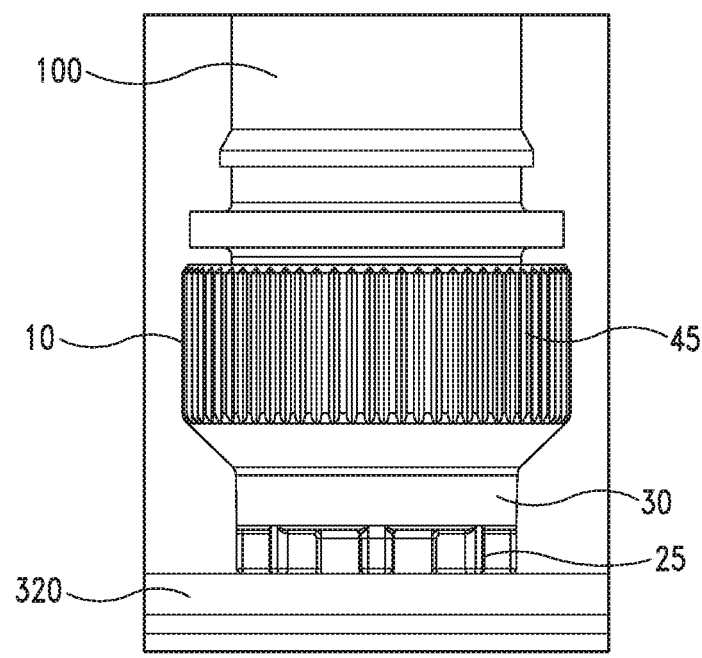
FIGS. 5A and 5B are close-up views of one embodiment of the sample collection and delivery apparatus of the present invention coupled with a microfluidic device.
Figure 5B:
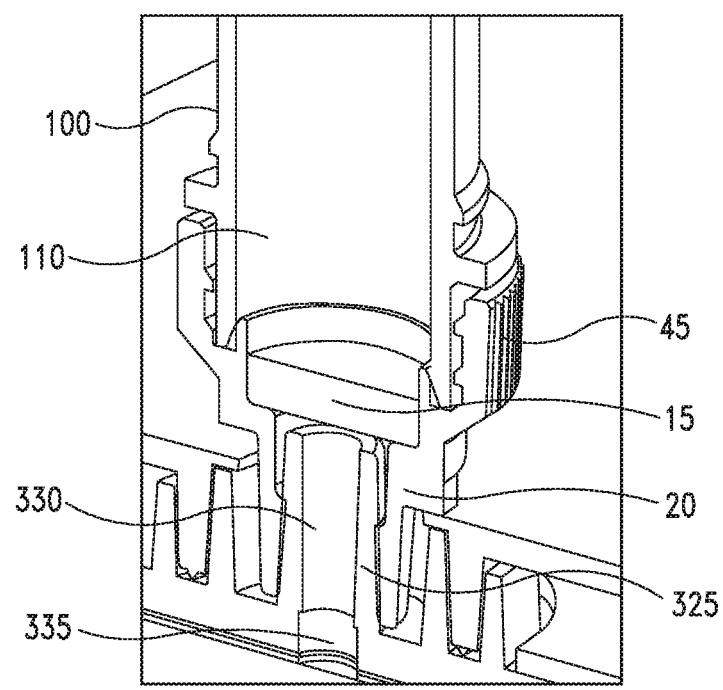

FIGS. 5A and 5B are exploded views depicting further details of the couplings between the sample tube, specimen collection and delivery apparatus, and microfluidic cartridge. FIG. 5A shows the exterior features of the sample housing 10, including the base portion 45, tapered mid-portion 30, and projecting ribs 25 with the projecting ribs in contact with the outboard portion 320 of the microfluidic cartridge and the sample tube 100 in an inverted orientation. FIG. 5B shows a cross-sectional view of the features depicted in FIG. 5A with the luer taper 20 of the closure housing coupled, or "mated to", the luer taper 325 of the outboard portion of the microfluidic device. The coupled luer tapers are in sealed contact and form a sample channel 330 that is in fluid communication with a microfluidic channel 335 of the cartridge. Under ambient laboratory conditions, the filter matrix 15 of the closure assembly forms a liquid barrier that prevents any specimen material in the sample tube from entering the sample channel. In operation, an external vacuum can be applied to the sample channel, for example, by the host instrument into which the inboard portion of the microfluidic cartridge is inserted. Under vacuum, liquid sample is drawn through the filter matrix into the sample channel, while particulate matter is retained in the specimen collection and delivery apparatus. Liquid sample then enters the microfluidic channel and is delivered into the cartridge for further processing and analysis, under control of the host instrument.

Figure 6:
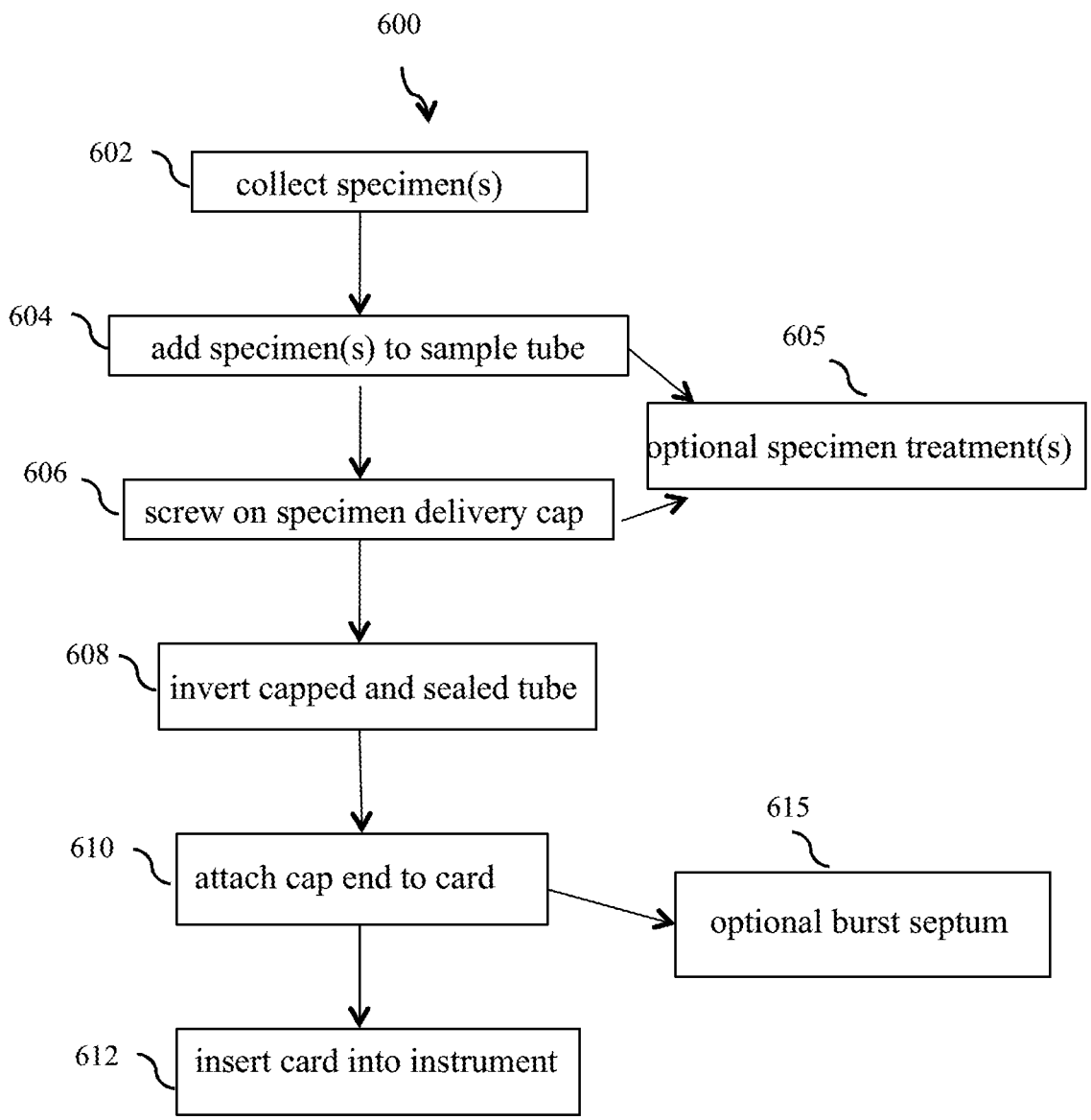
FIG. 6 is a block diagram of an illustrative sample collection and delivery method of the present invention.

FIG. 6 is a block diagram of an illustrative method 600 for using the specimen collection and delivery apparatus of the present invention to collect and deliver a clinical sample for analysis. Step 602 includes collecting one or more biological specimens from a patient or donor. The one or more specimen(s) can be collected by a laboratory technician, a doctor or nurse, and/or a patient or donor. The one or more specimen(s) can be any liquid, semi-liquid, or solid biosamples of tissues, discharges, or excretions, taken by swab, or needle or the like. In one embodiment, the one or more specimen(s) can be blood or a blood product. In another embodiment, the one or more specimen(s) can be feces. In yet another embodiment the one or more specimen(s) can be a tissue biopsy. In yet another embodiment, the one or more specimen(s) can include biopsies from different tissues from a patient suspected of having an infectious disease, such as tuberculosis. Step 604 includes adding the one or more specimen(s) to a sample tube. The one or more specimen(s) can be added by a pipette or blood dropper or by a swab that may have a breakable handle for selectively retaining the swab in the sample tube. Solid specimens can be added by any manual mean known in the art. Solid and/or semi-solid samples are preferentially added into sample tubes preloaded with buffer, diluent, or collection fluid, such as a sterile PBS and the like. Optional step 605 can include any of a number of treatment steps to facilitate preparation of sample for analysis, including addition of reagents to aid in the dissolution of the specimen and release of the analyte of interest and/or to inhibit degradation of the analyte of interest. Optional treatments can also include physical means to disrupt cells to release analytes of interest, such as addition of heat, sonication, or electroporation. In some embodiments, beater beads are used to aid in disruption of bacteria, such as *Mycobacterium tuberculosis*. Other optional treatments also include exposure to clotting agents or factors to separate the plasma fraction from whole blood specimens. Step 606 includes selective coupling of the specimen collection and delivery apparatus of the present invention, which can be referred to as a "specimen delivery cap" or "cap" for brevity. In one embodiment, the cap is screwed on to the sample tube to create a hermetic, pneumatically tight seal that prevents leakage of specimen and flow of external air into the sample tube. Step 608 includes inverting the capped and sealed sample tube. The filter matrix of the specimen collection and delivery apparatus prevents sample from leaking out of the cap and all specimen material is thus retained in the sealed sample tube. Step 610 includes attaching the capped end of the inverted sample tube to a microfluidic testing cartridge. Attachment is mediated through complementary luer tapers on the sample cap and microfluidic cartridge, which couple, or "mate" to form a sealed connection. The sealed connection creates a fluid channel between the specimen collection and delivery apparatus and the microfluidic device that is blocked by the filter matrix. Optional step 615 includes bursting a septum in the sample cap, which provides audible and/or tactile feedback to the end-user that the sample cap has been adequately attached to the microfluidic card. Step 612 includes inserting the microfluidic cartridge into a host instrument via an inboard cartridge portion. The host instrument controls pneumatic forces on the luer connection. When a sufficient vacuum is applied to the connection, liquid sample is drawn through the filter matrix and into the microfluidic cartridge for further processing and analysis, while particulate matter is retained in the filter. In some embodiments, the liquid sample passing through the filter matrix rehydrates internal control material impregnated in the filter, which is then solubilized in the liquid sample. The internal control material is thus subjected to all the same downstream processing and analysis steps as the sample material.

Figure 7A:
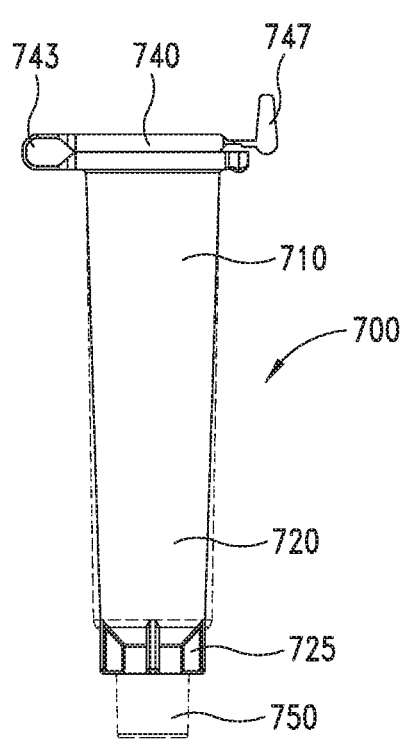
FIGS. 7A and 7B are perspective side views of another embodiment of the sample collection and delivery apparatus of the present invention.
Figure 7B:
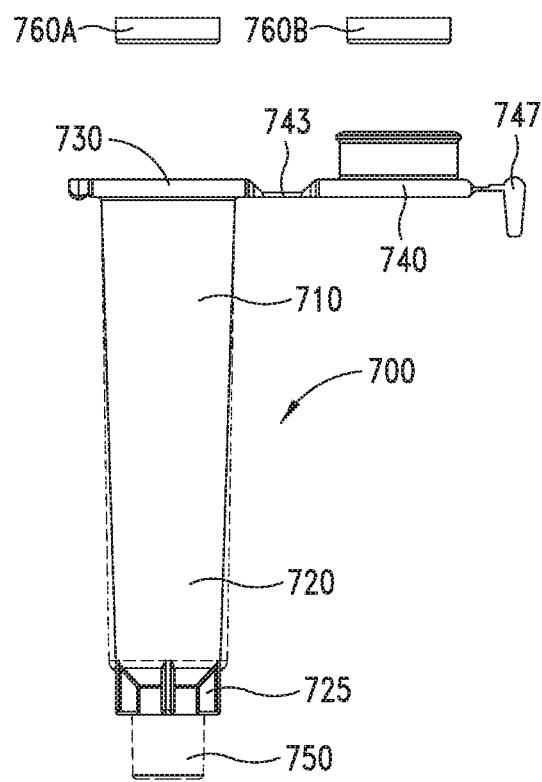

Referring now to FIGS. 7A and 7B, there are shown perspective side views of an alternative exemplary specimen collection and delivery apparatus 700 according to the present invention. The specimen collection and delivery apparatus 700 may also be referred to as a "sample tube". A sample tube, such as the specimen collection and delivery apparatus 700, can be any suitable sample tube for receiving, retaining, and delivering a medical specimen or sample, such as a bodily fluid, discharge, or tissue. The specimen collection and delivery apparatus includes a container having an upper portion 710 and a lower portion 720. The upper portion 710 has a generally cylindrical shape with a substantially circular cross-section with an upper opening 730. The lower portion 720 depends from the upper portion and has a generally conical shape with a lower open luer end 750. Together, the upper portion, the lower portion, and the luer end form an interior region 715 of the specimen collection and delivery apparatus. The lower portion 720 is configured to receive a filter matrix 760A. In one embodiment, the external surface of the lower portion 720 proximate to the luer end can be radially disposed with circumferential ribbed projections 725. The number and positioning of the ribbed projections is not obligatory to the invention and several possible alternatives of each are herein contemplated. The specimen collection and delivery apparatus 700 can be translucent and/or colored can may be any suitable size, e.g., any sizes used in standard clinical analysis, such as 2 mL. The specimen collection and delivery apparatus 700 can include a closure housing 740 disposed proximate to the upper opening 730. The closure housing can include any suitable structure for closing or sealing of the upper opening. The closure housing 740 can also be referred to as a "sample tube cap". In one embodiment, the closure housing 740 is configured to releasably or removably seal the upper opening. The closure housing can include a tab 747 for grasping and/or removing the closure housing from the upper opening. In one embodiment, a tab 747 can optionally aid in locking the closure housing into the upper opening. The closure housing can include a flexible hinge 743 to connect the closure housing 740 to the upper portion 710 of the sample tube. The closure housing can include an upper filter chamber 745 which can be configured to receive a filter matrix 760B. The upper filter chamber 745 and the filter matrix 760B are configured to "snap" fit inside the upper portion 710 of the sample tube when the upper opening 730 is sealed with the closure housing 740. The outer surface of the closure housing 740 is configured with a vent hole 749 to vent the interior portion of the sample tube to external atmosphere.

As described herein, filter matrices, 760A and 760B, are generally porous disc-shaped structures that are air permeable and liquid impermeable under ambient conditions. The filter matrices are configured such that a drop in atmospheric pressure (e.g. a $\Delta p$ of one psi) enables liquid sample to pass through the filters. When operably disposed within the closure housing 740, the filter matrix 760B functions to allow the passage of air while blocking the flow of liquid. In this manner, the filter matrix protects the end-user from contact with the specimen, while allowing for venting of the interior of the sample tube. When operably disposed within the lower portion 720 of the sample tube, the filter matrix 760A functions to block the flow of liquid sample out of the sample tube under standard laboratory conditions. In practice, application of vacuum force to the luer taper end 750 of the specimen collection and delivery apparatus draws the liquid phase of a collected specimen through the filter matrix. In contrast, any particulate matter larger than the pore size of the filter is retained and thus separated from the liquid phase. In some embodiments, as described herein, the filter matrix 760A can be impregnated with an internal assay control.

Figures 8A, 8B:
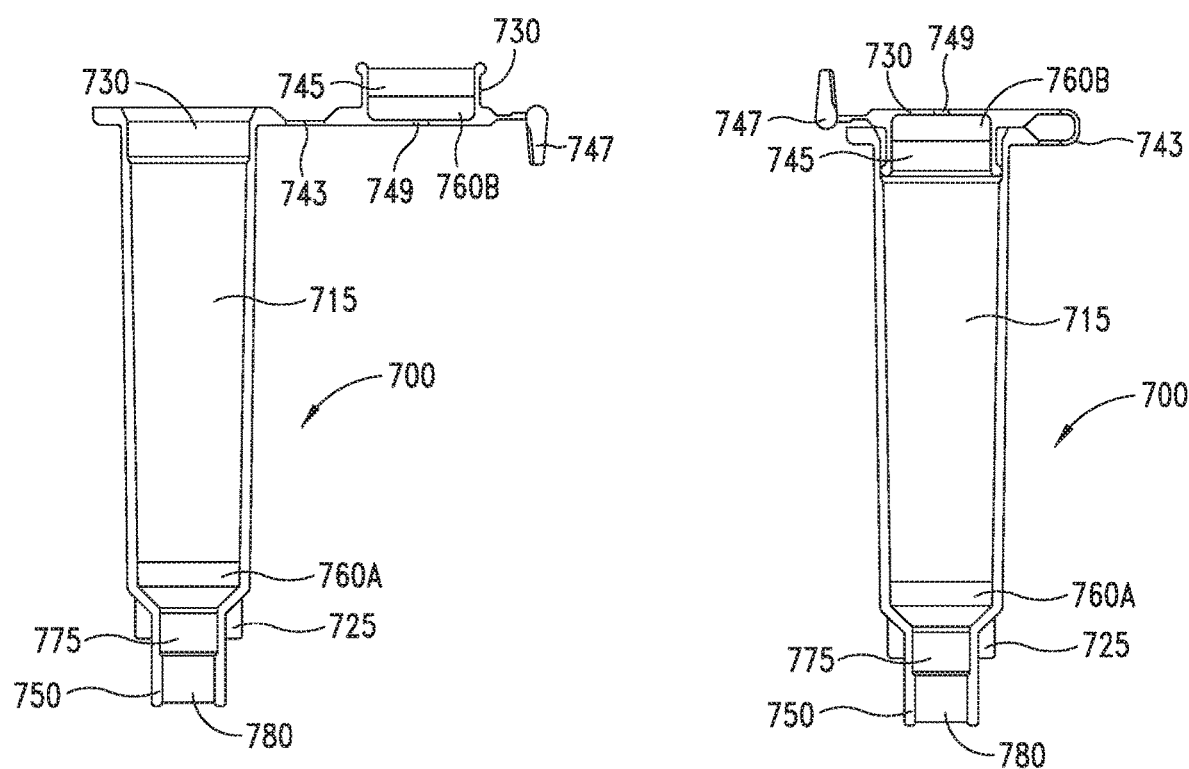
FIGS. 8A and 8B are cross-sectional side views of alternative embodiments of the sample collection and delivery apparatus of the present invention.

This arrangement of features of the specimen collection and delivery apparatus 700 is depicted in more detail in FIGS. 8A and 8B, which are cross-sectional views of alternative embodiments of the invention. FIG. 8A depicts the specimen collection and delivery apparatus 700 in an open configuration. FIG. 8B depicts the specimen collection and delivery apparatus 700 in a sealed, or closed configuration, with the filter chamber 745 and the filter matrix 760B positioned in the interior portion 715 of the apparatus. In this configuration, the filter chamber, interior portion of the apparatus, and the filter matrix are in fluid communication. The filter matrix 760A is in further fluid communication with the lower chamber 775 and the luer lumen 780. In an alternative embodiment of the invention, the specimen collection and delivery apparatus 700 can optionally include a septum disposed between the luer lumen 780 and the lower chamber 775. As disclosed herein, the septum is a burstable membrane that is disrupted when the luer taper end 780 is fixedly coupled to a complementary mating luer taper of a test device. In practice, bursting of the septum provides audible and/or tactile feedback to the end-user when the specimen collection and delivery system is operably coupled to a test device. As described herein, the test device can be a microfluidic cartridge.

Figure 9:
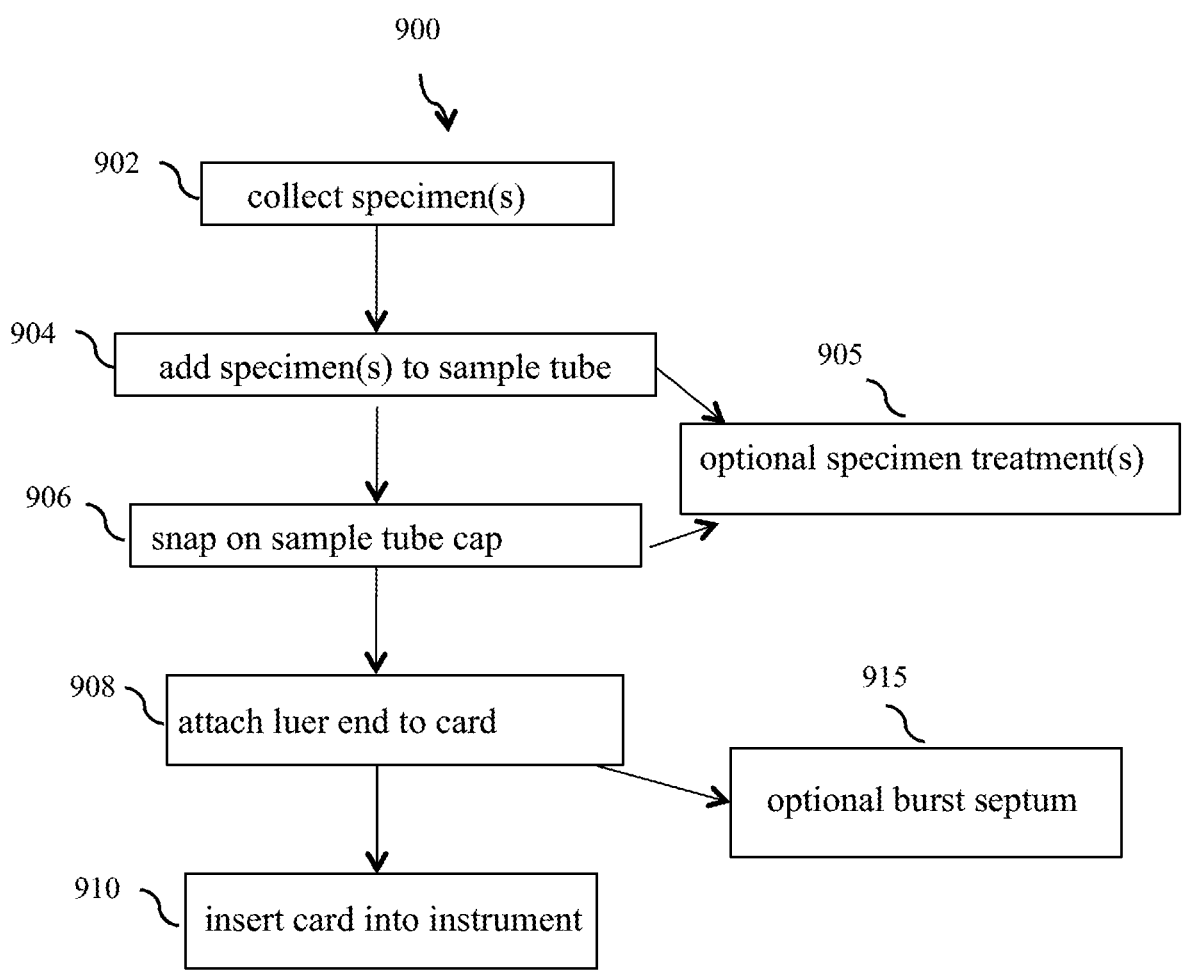
FIG. 9 is a block diagram of another illustrative sample collection and delivery method of the present invention.

FIG. 9 is a block diagram of an illustrative method 900 for using the specimen collection and delivery apparatus 700 to collect a clinical or other specimen. Step 902 includes collecting one or more biological specimens from a patient or donor. The one or more specimen(s) can be collected by a laboratory technician, a doctor or nurse, and/or a patient or donor. The one or more specimen(s) can be any liquid, semi-liquid, or solid biosamples of tissues, discharges, or excretions, taken by swab, or needle or the like. In one embodiment, the one or more specimen(s) can be blood or a blood product. In another embodiment, the one or more specimen(s) can be feces. In yet another embodiment the one or more specimen(s) can be a tissue biopsy. In yet another embodiment, the one or more specimen(s) can include biopsies from different tissues from a patient suspected of having an infectious disease, such as tuberculosis. Step 904 includes adding the one or more specimen(s) to the interior space of the specimen collection and delivery apparatus. The one or more specimen(s) can be added by a pipette or blood dropper or by a swab that can have a breakable handle for selectively retaining the swab in the sample tube. Solid specimens can be added by any manual mean known in the art. Solid and/or semi-solid samples are preferentially added into sample tubes pre-loaded with buffer, diluent, or collection fluid, such as a sterile PBS and the like. Optional step 905 includes any of a number of treatment steps to facilitate preparation of sample for analysis, including addition of reagents to aid in the dissolution of the specimen and release of the analyte of interest and/or to inhibit degradation of the analyte of interest. Optional treatments can also include physical means to disrupt cells to release analytes of interest, such as addition of heat, sonication, or electroporation. Step 906 includes selective coupling of the closure assembly of the present invention. In one embodiment, the closure assembly or "cap" is snapped on to the sample tube to create a tight seal that prevents leakage of specimen. Air can be vented from the tube through the vent hole. Step 908 includes attaching the luer end of the sample tube to a test device, e.g., microfluidic card or cartridge. Attachment is mediated through complementary luer tapers on the sample tube and the microfluidic card, which couple, or "mate" to form a sealed connection. The sealed connection creates a fluid channel between the sample tube and the microfluidic device that is blocked by the filter matrix in the lower portion of the sample tube. Optional step 915 can include bursting a septum in the sample tube, which provides audible and/or tactile feedback to the user that the sample tube has been successfully attached to the microfluidic card. Step 910 includes inserting the microfluidic card into a host instrument via an inboard card portion. The host instrument can control pneumatic forces on the luer connection, and by creating a vacuum, draw liquid sample through the filter matrix and into the microfluidic card for further processing and analysis, while particulate matter is retained in the filter.

Exemplary embodiments include, but are not limited to the following:

Embodiment 1

A sample collection and delivery apparatus, comprising:
a closure housing including:
a base portion configured for selective removable coupling to a sample tube, a tapered mid portion, and an open luer end configured for receiving a complementary luer of a test device; and a filter matrix disposed therein.

Embodiment 2

The sample collection and delivery apparatus of embodiment 1, wherein the filter matrix is air permeable and liquid impermeable at atmospheric pressure and configured to block the flow of sample through the open luer end.

Embodiment 3

The sample collection and delivery apparatus of embodiment 2, wherein the filter matrix is air permeable and liquid permeable under reduced atmospheric pressure and configured to enable the flow of sample though the open luer end.

Embodiment 4

The sample collection and delivery apparatus of embodiment 3, wherein the reduced atmospheric pressure is around one pound per square inch.

Embodiment 5

The sample collection and delivery apparatus of embodiment 1, wherein the filter matrix is disposed in the interior of the tapered mid portion.

Embodiment 6

The sample collection and delivery apparatus of embodiment 1, wherein the filter matrix is comprised of a porous material selected from the group consisting of a hydrophobic porous material, a hydrophilic porous material, an oleophobic porous material, and an oleophilic porous material.

Embodiment 7

The sample collection and delivery apparatus of embodiment 6, wherein the filter matrix is comprised of a hydrophobic porous material.

Embodiment 8

The sample collection and delivery apparatus of embodiment 7, wherein the hydrophobic porous material is a polymeric material.

Embodiment 9

The sample collection and delivery apparatus of embodiment 1, wherein the filter matrix has a pore size of from around 50 µm to around 100 µm and a thickness of around 1000 µm to around 2000 µm.

Embodiment 10

The sample collection and delivery apparatus of embodiment 1, wherein the filter matrix is impregnated with an internal assay control.

Embodiment 11

The sample collection and delivery apparatus of embodiment 10, wherein the internal assay control comprises a natural nucleic acid sequence or a non-natural nucleic acid sequence.

Embodiment 12

The sample collection and delivery apparatus of embodiment 1, further comprising circumferential projections radially disposed between the tapered mid portion and the luer end.

Embodiment 13

The sample collection and delivery apparatus of embodiment 1, wherein the base portion includes an internal threaded portion configured for removable coupling with a complementary threaded portion of a sample tube.

Embodiment 14

The sample collection and delivery apparatus of embodiment 1, wherein the closure housing is selectively removably coupled to a sample tube.

Embodiment 15

The sample collection and delivery apparatus of embodiment 14, wherein the volume of the sample tube is around 2 mL.

Embodiment 16

A method of collecting and delivering a test sample to a microfluidic cartridge, comprising the steps of:
a) obtaining a test sample from an individual suspected of having a condition;
b) providing a sample tube with a first open end;
c) disposing the test sample in the sample tube;
d) coupling the sample collection and delivery apparatus of embodiment 1 to the sample tube;
e) inverting the sample tube;
f) coupling the luer taper end of the sample collection and delivery apparatus to a complementary luer taper end on the microfluidic cartridge to create a luer channel;
g) inserting the microfluidic cartridge into a host instrument; and
h) instructing the host instrument to apply a vacuum to the luer channel.

Embodiment 17

A sample collection and delivery apparatus, comprising: a sample tube having an interior portion configured to contain a test specimen, an upper portion with an opening to the interior portion configured to receive the specimen, a lower portion with a first filter matrix disposed therein, and an open luer end opposite the opening to the interior portion, wherein the first filter matrix is configured to block the flow of the specimen through the open luer end; and a closure housing configured for sealing the opening, including a filter chamber with a second filter matrix disposed therein, a tab configured for user manipulation, a flexible hinge configured to couple the closure housing to the sample tube, and, optionally, a vent hole.

Embodiment 18

The sample collection and delivery apparatus of embodiment 17, wherein the first filter matrix is air permeable and liquid impermeable at atmospheric pressure.

Embodiment 19

The sample collection and delivery apparatus of embodiment 17, wherein the first filter matrix is air permeable and liquid permeable under reduced atmospheric pressure and configured to enable the flow of liquid specimen through the luer end.

Embodiment 20

The sample collection and delivery apparatus of embodiment 19, wherein the reduced atmospheric pressure is around one pound per square inch.

Embodiment 21

The sample collection and delivery apparatus of embodiment 16, wherein the filter matrix is comprised of a porous material selected from the group consisting of a hydrophobic porous material, a hydrophilic porous material, an oleophobic porous material, and an oleophilic porous material.

Embodiment 22

The sample collection and delivery apparatus of embodiment 21, wherein the filter matrix is comprised of a hydrophobic porous material.

Embodiment 23

The sample collection and delivery apparatus of embodiment 22, wherein the hydrophobic porous material is a polymeric material.

Embodiment 24

The sample collection and delivery apparatus of embodiment 16, wherein the first filter matrix has a pore size of from around 50 µm to around 100 µm and a thickness of around 1000 µm to around 2000 µm.

Embodiment 25

The sample collection and delivery apparatus of embodiment 16, wherein the first filter matrix is impregnated with an internal assay control.

Embodiment 26

The sample collection and delivery apparatus of embodiment 25, wherein the internal assay control comprises a natural or a non-natural nucleic acid sequence.

Embodiment 27

The sample collection and delivery apparatus of embodiment 16, further comprising circumferential projections radially disposed between the lower portion and the luer end.

Embodiment 28

A method of collecting and delivering a test sample to a microfluidic cartridge, comprising the steps of:
a) obtaining a test specimen from an individual suspected of having a condition;
b) disposing the test specimen in the sample collection and delivery apparatus of embodiment 16;
c) coupling the luer taper end of the sample collection and delivery apparatus to a complementary luer taper end on the microfluidic cartridge to create a luer channel;
d) inserting the microfluidic cartridge into a host instrument; and
e) instructing the host instrument to apply a vacuum to the luer channel.

It should be understood, of course, that the foregoing relates to exemplary embodiments of the disclosure and that one or more modifications may be made without departing from the spirit and scope of the disclosure as set forth in the following claims:

The various implementations described above can be combined to provide further implementations. All of the U.S. patents, U.S. patent application publications, U.S. patent applications, foreign patents, foreign patent applications and non-patent publications referred to in this specification and/or listed in the Application Data Sheet, including but not limited to U.S. provisional patent application Ser. No. 62/154,509 filed Apr. 29, 2015 are incorporated herein by reference, in their entirety.

What is claimed is:

1. A sample collection and delivery apparatus, comprising:
a closure housing including:
a base portion configured for selective removable coupling to a sample tube, a tapered mid portion, and an open luer end configured for receiving a complementary luer of a test device; and
a filter matrix, impregnated with an internal assay control, disposed within the closure housing;
wherein, at atmospheric pressure, the filter matrix is air permeable and liquid impermeable and configured to block the flow of sample through the open luer end; and
wherein, under reduced atmospheric pressure, the filter matrix is air permeable and liquid permeable and configured to enable the flow of sample though the open luer end.

2. The sample collection and delivery apparatus of claim 1, wherein the reduced atmospheric pressure is one pound per square inch.

3. The sample collection and delivery apparatus of claim 1, wherein the filter matrix is disposed in the interior of the tapered mid portion.

4. The sample collection and delivery apparatus of claim 1, wherein the filter matrix is comprised of a porous material selected from the group consisting of a hydrophobic porous material, a hydrophilic porous material, an oleophobic porous material, and an oleophilic porous material.

5. The sample collection and delivery apparatus of claim 4, wherein the filter matrix is comprised of a hydrophobic porous material.

6. The sample collection and delivery apparatus of claim 5, wherein the hydrophobic porous material is a polymeric material.

7. The sample collection and delivery apparatus of claim 1, wherein the filter matrix has a pore size of from 50 µm to 100 µm and a thickness of from 1000 µm to 2000 µm.

8. The sample collection and delivery apparatus of claim 1, wherein the internal assay control comprises a natural nucleic acid sequence or a non-natural nucleic acid sequence.

9. The sample collection and delivery apparatus of claim 1, further comprising circumferential projections radially disposed between the tapered mid portion and the open luer end.

10. The sample collection and delivery apparatus of claim 1, wherein the base portion includes an internal threaded portion configured for removable coupling with a complementary threaded portion of a sample tube.

11. The sample collection and delivery apparatus of claim 1, wherein the closure housing is selectively removably coupled to a sample tube.

12. The sample collection and delivery apparatus of claim 11, wherein the volume of the sample tube is 2 mL.

13. The sample collection and delivery apparatus of claim 1 wherein the internal assay control produces color upon hydration.

14. The sample collection and delivery apparatus of claim 1 wherein the internal assay control is present at a concentration near a lower limit of detection of an assay.

15. The sample collection and delivery apparatus of claim 1 wherein the internal assay control is printed on the filter matrix.

16. A method of collecting and delivering a test sample to a microfluidic cartridge, comprising:
   a) obtaining a test sample from an individual suspected of having a condition;
   b) providing a sample tube with a first open end;
   c) disposing the test sample in the sample tube;
   d) coupling the sample collection and delivery apparatus of claim 1 to the sample tube;
   e) inverting the sample tube;
   f) coupling the open luer end of the sample collection and delivery apparatus to a complementary luer end on the microfluidic cartridge to create a luer channel;
   g) inserting the microfluidic cartridge into a host instrument; and
   h) instructing the host instrument to apply a vacuum to the luer channel.

* * * * *